US010525043B2

(12) United States Patent
Bhagwat et al.

(10) Patent No.: US 10,525,043 B2
(45) Date of Patent: *Jan. 7, 2020

(54) COMPOSITIONS COMPRISING ANTIBACTERIAL AGENT AND TAZOBACTAM

(75) Inventors: Sachin Subhash Bhagwat, Aurangabad (IN); Mohammad Alam Jafri, Aligarh (IN); Mahesh Vithalbhai Patel, Aurangabad (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/111,627

(22) PCT Filed: Aug. 1, 2011

(86) PCT No.: PCT/IB2011/053398
§ 371 (c)(1),
(2), (4) Date: Dec. 13, 2013

(87) PCT Pub. No.: WO2012/164358
PCT Pub. Date: Dec. 6, 2012

(65) Prior Publication Data
US 2014/0162995 A1 Jun. 12, 2014

(30) Foreign Application Priority Data
May 28, 2011 (IN) .......... 1587/MUM/2011

(51) Int. Cl.
*A61K 31/431* (2006.01)
*A61K 31/546* (2006.01)
*A61K 31/43* (2006.01)
*A61K 31/407* (2006.01)

(52) U.S. Cl.
CPC .......... *A61K 31/431* (2013.01); *A61K 31/407* (2013.01); *A61K 31/43* (2013.01); *A61K 31/546* (2013.01); *Y02A 50/473* (2018.01)

(58) Field of Classification Search
USPC ....................................... 514/192
See application file for complete search history.

(56) References Cited

U.S. PATENT DOCUMENTS

2010/0029604 A1* 2/2010 Prezelj .............. A61K 31/403
514/196
2010/0197650 A1 8/2010 Biek

FOREIGN PATENT DOCUMENTS

| CN | 1565455 A | | 1/2005 |
|---|---|---|---|
| CN | 1565456 | * | 1/2005 |
| CN | 1565456 A | | 1/2005 |
| WO | WO2007086011 A1 | | 8/2007 |
| WO | WO2007086014 A1 | | 8/2007 |

OTHER PUBLICATIONS

Wilson, Diagn Microbiol Infect Dis. vol. 31, pp. 473-477; publication year: 1998.*
Human Translation of Zhang et al. CN1565456. Schreiber Translations, Inc. received by the USPTO Feb. 2016.*
Endimian et al., Characterization of blaKPC—containing Klebsiella pneumoniae isolates detected in different institutions in the Eastern USA. Journal of Antimicrobial Chemotherapy. 63 3: 427-437, (2009).
Jones et al. Antimicrobial spectrum of cefpirome combined with tazobactam against the Bacteroides fragilis group. Diagn Microbiol Infect Dis. Sep.-Oct. 1990;13(5):371-3.
Andrea Endimiani. Characterization of blaKPC—containing Klebsiella pneumoniae isolates detected in different institutions in the Eastern USA.J. Antimicrob. Chemother. (2009) 63 (3): 427-437.
Sugar et al., Interactions of Itraconazole with Amphotericin B in the Treatment of Murine Invasive Candidiasis. The Journal of Infectious Diseases 1988, vol. 177, pp. 1660-1663.
Maesaki et al. Effects of antifungal agent combinations administered simultaneously and sequentially against Aspergillus fumigatus. Antimicrobial Agents and Chemotherapy, Dec. 1994, pp. 2843-2845.
Bergogne-Berezin. Mechanisms and clinical relevance of antagonism between beta-lactam antibiotics. Chemioterapia. Feb. 1985;4(1):47-52.
Ventola. The Antibiotic Resistance Crisis. Part 1: Causes and Threats. P T. Apr. 2015; 40(4): 277-283.
Penchovsky. Designing drugs that overcome antibacterial resistance: where do we and what should we do? Expert Opin Drug Discov. Jun. 2015;1 (6):631-650.
Fleming. Penicillin Nobel Lecture, Dec. 11, 1945.
O'Neill. Tackling drug-resistant infections globally: final report and recommendations. The review on antimicrobial resistance May 2016. 84 pages.
Blaser et al. Comparative study with enoxacin and netilmicin in a pharmacodynamic model to determine importance of ratio of antibiotic peak concentration to MIC for bactericidal activity and emergence of resistance. Antimicrob Agents Chemother (1987). 31:1054-1060.
Dudley et al. Pharmacokinetics and pharmacodynamics of intravenous ciprofloxacin. Studies in vivo and in an in vitro dynamic model. Am J Med. (1987). 82:363-368.
Borriello et al., Arginine or nitrate enhances antibiotic susceptibility of Pseudomonas aeruginosa in biofilms. Antimicrob Agents Chemother. Jan. 2006;50(1):382-3844).
Sader et al. Antimicrobial Activity of High-Proportion Cefepime-Tazobactam (WCK 4282) against a Large Number of Gram-Negative Isolates Collected Worldwide in 2014. Antimicrob Agents Chemother. Mar. 24, 2017;61(4). Print Apr. 2017.

* cited by examiner

*Primary Examiner* — Katherine Peebles
(74) *Attorney, Agent, or Firm* — Bio Intellectual Propertiy Services LLC (Bio IPS); O. (Sam) Zaghmout

(57) ABSTRACT

A pharmaceutical composition comprising antibacterial agent and tazobactam, wherein the ratio of tazobactam to the antibacterial agent in the composition is in the range of from about 0.5 to about 2 gram of tazobactam per gram of the antibacterial agent, are disclosed.

3 Claims, No Drawings

COMPOSITIONS COMPRISING ANTIBACTERIAL AGENT AND TAZOBACTAM

This application claims the benefit of Indian Patent Application No. 1587/MUM/2011 filed on May 28, 2011, the disclosure of which are incorporated herein by reference in its entirety as if fully rewritten herein. All references including patents, patent applications, and literature cited in the specification are expressly incorporated herein by reference in their entirety.

FIELD OF THE INVENTION

The invention relates to antibacterial compositions.

BACKGROUND OF THE INVENTION

The World Health Organization Fact Sheet (No. 194, revised January 2002) notes that the bacterial infections which contribute most to human diseases are also those in which emerging microbial resistance is most evident: diarrhoeal diseases, respiratory tract infections, meningitis, sexually transmitted infections, and hospital-acquired infections. Some important examples of bacteria resistant to typical antibacterial agents include: penicillin-resistant *Streptococcus pneumoniae*, vancomycin-resistant enterococci, and methicillin-resistant *Staphylococcus aureus*. However β-lactam, fluoroquinolones and aminoglycoside resistance in Gram negatives is currently posing the greatest challenge to clinicians. β-lactam antibiotics have conventionally remained the mainstay of therapy for the management of wide range of Gram-negative infections, including those caused by *Klebsiella, Escherichia coli, Enterobacter, Serratia, P. aeruginosa* etc.

The problem of emerging drug-resistance in bacteria is often tackled by switching to next-line of antibacterial agents, which can be more expensive and sometimes more toxic. However, even this may not be a permanent solution and the bacteria often develop resistance to the newer antibacterial agents in due course. Bacteria are particularly efficient in developing resistance, because of their ability to multiply very rapidly and pass on the resistance genes as they replicate.

Several antibacterial combinations have been studied in the prior art including those by Mayer et al. (Investigation of the aminoglycosides, fluoroquinolones and third-generation cephalosporin combinations against clinical isolates of *Pseudomonas* spp. J. Antimicrob. Chemother., 43, 651-657, 1999); Gradelski et al. (Synergistic activities of gatifloxacin in combination with other antibacterial agents against clinical isolates of *Pseudomonas aeruginosa* and related species. Antimicrob. Agents Chemother., 45, 3220-3222, 2001); Fish et al. (Synergistic activity of cephalosporins plus fluoroquinolones against *Pseudomonas aeruginosa* with resistance to one or both drugs. J. Antimicrob. Chemother., 50, 1045-1049, 2002) and Davis et al. (In vitro activity of gatifloxacin alone and in combination with cefepime, meropenem, piperacillin and gentamicin against multidrug-resistant organisms, J. Antimicrob. Chemother., 51, 1203-1211, 2003). Fish et al. found combination of cefepime or ceftazidime with ciprofloxacin, levofloxacin, gatifloxacin or moxifloxacin synergistic against 10 clinical *Pseudomonas aeruginosa* strains including those most resistant to both cephalosporins and fluoroquinolones. In another study, N. Sivagurunathan et al. (Synergy of gatifloxacin with cefoperazone and cefoperazone-sulbactam against resistant strains of *Pseudomonas aeruginosa*. J. Medical Microb., 57, 1514-1517, 2008) obtained in vitro synergy with gatifloxacin and cefoperazone and gatifloxacin-cefoperazone-sulbactam combination against resistant strains of *Pseudomonas aeruginosa*. In few cases, these antibiotic combinations have also been successfully employed as an effective treatment for *Pseudomonas aeruginosa* nosocomial infections (Al-Hasan et. al, β-Lactam and Fluoroquinolone combination antibiotic therapy for bateremia caused by Gram-negative bacilli. Antimicrob. Agents Chemother., 53(4), 1386-1394, 2009).

Bacteria use several mechanisms to acquire resistance to antibacterial agents including, such as for example, drug inactivation or modification (e.g. enzymatic deactivation of Penicillin G in some penicillin-resistant bacteria through the production of β-lactamases), alteration of target site (e.g. alteration of PBP, the binding target site of penicillins in MRSA and other penicillin-resistant bacteria), alteration of metabolic pathway (e.g. some sulfonamide-resistant bacteria do not require para-aminobenzoic acid (PABA), an important precursor for the synthesis of folic acid and nucleic acids in bacteria inhibited by sulfonamides) or reduced accumulation of antibacterial agents through efflux pumps (e.g. by decreasing permeability and/or increasing active efflux of the antibacterial agents across the cell surface).

There are four primary mechanisms by which bacteria can overcome β-lactam antibiotics: (i) production of β-lactamases; (ii) mutations in the target PBPs; (iii) decreased expression of outer membrane proteins/porins; and (iv) efflux pumps. Production of β-lactamases is the main mechanism of resistance to this class of antibiotic. Introduction of extended spectrum ⊖-lactams during 1980s were responded by Gram-negative organisms with the production of extended spectrum β-lactamases (ESBLs). ESBLs are plasmid mediated β-lactamases, known as extended spectrum, because they are able to hydrolyze a broader spectrum of β-lactam antibiotics including third and fourth generation cephalosporins.

Resistance to β-lactams, β-lactams-β-lactamsase-inhibitors, cephalosporins and monobactam is wide spread. Such resistance challenges the ability to treat serious urinary tract infection, respiratory tract infections and blood stream infections. Internationally, the prevalence of ESBL in *Klebsiella* and *E. coli* is in the range of 30-50% depending upon the geographical location. For ESBLs, carbapenem therapy is most widely used in the clinical settings today. Presently, all strains identified as inhibitor resistant ESBLs are treated only by carbapenems. This extensive and widespread use of carbapenems has triggered the selection of carbapenem resistant strains.

Therefore, there is a need for development of compositions capable of acting against ESBLs, which are currently resistant to available β-lactam-β-lactamase inhibitor (and can only be treated by carbapenems). Surprisingly, it has been found that a pharmaceutical composition comprising effective amount of an antibacterial agent and tazobactam or a pharmaceutically acceptable salt thereof, in a specific ratio of tazobactam to the antibacterial agent in the composition, exhibits unexpectedly improved antibacterial efficacy, even against highly resistant ESBL producing gram negative pathogens.

SUMMARY OF THE INVENTION

Accordingly, there are provided pharmaceutical compositions comprising effective amount of an antibacterial agent and tazobactam or a pharmaceutically acceptable salt thereof.

In one general aspect, there is provided a pharmaceutical composition comprising effective amount of (a) at least one antibacterial agent selected from cefepime, cefpirome, ceftobiprole, ceftaroline, cefclidine, cefluprenam, cefoselis, cefozopran, cefquinome, moxalactam, flomoxef, biapenem, panipenem, doripenem, ertapenem, meropenem, imipenem, razupenem, temocillin, CXA-101, or a pharmaceutically acceptable salt thereof; and (b) tazobactam or a pharmaceutically acceptable salt thereof, wherein the ratio of tazobactam to the antibacterial agent in the composition is in the range of from about 0.5 to about 2 gram of tazobactam per gram of the antibacterial agent.

In another general aspect, there is provided a method for treatment or control of bacterial infection in a subject, said method comprising administering to said subject a therapeutically effective amount of a pharmaceutical composition comprising effective amount of (a) at least one antibacterial agent selected from cefepime, cefpirome, ceftobiprole, ceftaroline, cefclidine, cefluprenam, cefoselis, cefozopran, cefquinome, moxalactam, flomoxef, biapenem, panipenem, doripenem, ertapenem, meropenem, imipenem, razupenem, temocillin, CXA-101, or a pharmaceutically acceptable salt thereof; and (b) tazobactam or a pharmaceutically acceptable salt thereof, wherein the ratio of tazobactam to the antibacterial agent in the composition is in the range of from about 0.5 to about 2 gram of tazobactam per gram of the antibacterial agent.

In another general aspect, a pharmaceutical composition comprising effective amount of (a) at least one antibacterial agent selected from cefepime, cefpirome, ceftobiprole, ceftaroline, cefclidine, cefluprenam, cefoselis, cefozopran, cefquinome, moxalactam, flomoxef, biapenem, panipenem, doripenem, ertapenem, meropenem, imipenem, razupenem, temocillin, CXA-101, or a pharmaceutically acceptable salt thereof; and (b) tazobactam or a pharmaceutically acceptable salt thereof, wherein the ratio of tazobactam to the antibacterial agent in the composition is in the range of from about 0.5 to about 2 gram of tazobactam per gram of the antibacterial agent, is used in treatment or control of bacterial infection in a subject.

In another general aspect, there is provided a pharmaceutical composition comprising effective amount of (a) cefepime or a pharmaceutically acceptable salt thereof; and (b) tazobactam or a pharmaceutically acceptable salt thereof, wherein the ratio of tazobactam to cefepime in the composition is in the range of from about 0.5 to about 2 gram of tazobactam per gram of cefepime.

In yet another general aspect, there is provided a method for treatment or control of bacterial infection in a subject, said method comprising administering to said subject a therapeutically effective amount of a pharmaceutical composition comprising effective amount of (a) cefepime or a pharmaceutically acceptable salt thereof; and (b) tazobactam or a pharmaceutically acceptable salt thereof, wherein the ratio of tazobactam to cefepime in the composition is in the range of from about 0.5 to about 2 gram of tazobactam per gram of cefepime.

In still another general aspect, a pharmaceutical composition comprising effective amount of (a) cefepime or a pharmaceutically acceptable salt thereof; and (b) tazobactam or a pharmaceutically acceptable salt thereof, wherein the ratio of tazobactam to cefepime in the composition is in the range of from about 0.5 to about 2 gram of tazobactam per gram of cefepime, is used in treatment or control of bacterial infection in a subject.

In yet another general aspect, there is provided a pharmaceutical composition comprising effective amount of (a) cefpirome or a pharmaceutically acceptable salt thereof; and (b) tazobactam or a pharmaceutically acceptable salt thereof, wherein the ratio of tazobactam to cefpirome in the composition is in the range of from about 0.5 to about 2 gram of tazobactam per gram of cefpirome.

In another general aspect, there is provided a method for treatment or control of bacterial infection in a subject, said method comprising administering to said subject a therapeutically effective amount of a pharmaceutical composition comprising effective amount of (a) cefpirome or a pharmaceutically acceptable salt thereof; and (b) tazobactam or a pharmaceutically acceptable salt thereof, wherein the ratio of tazobactam to cefpirome in the composition is in the range of from about 0.5 to about 2 gram of tazobactam per gram of cefpirome In another general aspect, a pharmaceutical composition comprising effective amount of (a) cefpirome or a pharmaceutically acceptable salt thereof; and (b) tazobactam or a pharmaceutically acceptable salt thereof, wherein the ratio of tazobactam to cefpirome in the composition is in the range of from about 0.5 to about 2 gram of tazobactam per gram of cefpirome, is used in treatment or control of bacterial infection in a subject.

The details of one or more embodiments of the inventions are set forth in the description below. Other features, objects and advantages of the inventions will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise.

The inventors have surprisingly discovered that a pharmaceutical composition comprising effective amount of an antibacterial compound and tazobactam or a pharmaceutically acceptable salt thereof, in a specific ratio of tazobactam to the antibacterial compound in the composition, exhibits unexpectedly improved antibacterial efficacy, even against highly resistant ESBL producing gram negative pathogens.

The term "infection" as used herein includes presence of bacteria, in or on a subject, which, if its growth were inhibited, would result in a benefit to the subject. As such, the term "infection" in addition to referring to the presence of bacteria also refers to normal flora, which are not desirable. The term "infection" includes infection caused by bacteria.

The term "treat", "treating" or "treatment" as used herein refers to administering a pharmaceutical composition for prophylactic and/or therapeutic purposes. The term "prophylactic treatment" refers to treating a subject who is not yet infected, but who is susceptible to, or otherwise at a risk of infection. The term "therapeutic treatment" refers to administering treatment to a subject already suffering from infection.

The term "administration" or "administering" includes delivery to a subject, including for example, by any appropriate method, which serves to deliver the composition or it's active ingredients to the site of the infection. The method of administration can vary depending on various factors, such as for example, the components of the pharmaceutical composition, the site of the potential or actual infection, the microorganism involved, severity of the infection, age and physical condition of the subject. Some non-limiting examples of ways to administer a composition or a compound to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In case of a pharmaceutical composition comprising more than one active ingredient, one of way of administering such composition is by admixing the active ingredients (e.g. in the form of a suitable unit dosage form such as tablet, capsule, solution, powder etc.) and then administering the dosage form. Alternatively, the active ingredients may also be administered separately (simultaneously or one after the other) as long as these ingredients reach beneficial therapeutic levels such that the composition as a whole provides a synergistic effect.

The term "therapeutically effective amount" or "effective amount" as used herein refers to an amount, which has a therapeutic effect or is the amount required to produce a therapeutic effect in a subject. For example, a therapeutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The therapeutic amount depends on several factors, including but not limited to, the microorganism involved, characteristics of the subject (for example height, weight, sex, age and medical history), severity of infection and the particular type of the antibacterial agent used. For prophylactic treatments, a therapeutically or prophylactically effective amount is that amount which would be effective to prevent a microbial infection.

The term "growth" as used herein refers to a growth of microorganisms and includes reproduction or population expansion of the microorganism. The term also includes maintenance of on-going metabolic processes of a microorganism, including processes that keep the microorganism alive.

The term "synergistic" or "synergy" as used herein refers to the interaction of two or more agents so that their combined effect is greater than their individual effects.

The term "antibacterial agent" as used herein refers to a compound capable of inhibiting, reducing or preventing growth of bacteria capable of inhibiting or reducing ability of a bacteria to produce infection in a host; or capable of inhibiting or reducing ability of bacteria to multiply or remain infective in the environment. The term "antibacterial agent" also refers to compounds capable of decreasing infectivity or virulence of bacteria. Antibacterial agents according to this invention include antibiotic agents.

A "carrier" or "excipient" is a compound or material used to facilitate administration of a compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

The term "CXA-101" as used herein refers to Ceftolozane (CAS Registry No.: 689293-68-3; Chemical Name: (6R, 7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methyl ethoxy)imino]acetyl}amino)-8-oxo-5-thia-1-azabicyclo [4.2.0]oct-2-ene-2-carboxylate). CXA-101 has a chemical structure as given Formula (I), below:

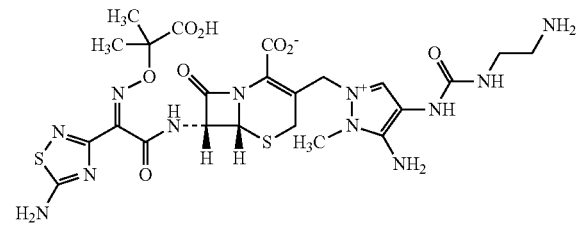

Formula (I)

A person of skills in the art would appreciate that various active compounds described herein can exist and are used in as their pharmaceutically acceptable salts, pro-drugs, metabolites, esters, ethers, hydrates, polymorphs, solvates, complexes, enantiomers, adducts or other pharmaceutically acceptable derivative. A reference to compounds, therefore, is intended to include such pharmaceutically acceptable salts, pro-drugs, metabolites, esters, ethers, hydrates, polymorphs, solvates, complexes, enantiomers, adducts or their any other pharmaceutically acceptable derivative. For example, the terms "antibacterial agents", "cefepime" or "cefpirome" includes their pharmaceutically acceptable salts, pro-drugs, metabolites, esters, ethers, hydrates, polymorphs, solvates, complexes, enantiomers, adducts or their any other pharmaceutically acceptable derivative.

In one general aspect, there is provided a pharmaceutical composition comprising effective amount of (a) at least one antibacterial agent selected from cefepime, cefpirome, ceftobiprole, ceftaroline, cefclidine, cefluprenam, cefoselis, cefozopran, cefquinome, moxalactam, flomoxef, biapenem, panipenem, doripenem, ertapenem, meropenem, imipenem, razupenem, temocillin, CXA-101 or a pharmaceutically acceptable salt thereof; and (b) tazobactam or a pharmaceutically acceptable salt thereof, wherein the ratio of tazobactam to the antibacterial agent in the composition is in the range of from about 0.5 to about 2 gram of tazobactam per gram of the antibacterial agent.

Both, the antibacterial agent and tazobactam may be present in the composition in their free forms or in the form of their pharmaceutically acceptable salts, pro-drugs, metabolites, esters, ethers, hydrates, polymorphs, solvates, complexes, enantiomers, adducts or in the form of their any other pharmaceutically acceptable derivative. The specified ratio of the antibacterial agent and tazobactam in the composition is calculated on the basis of their free forms. For example, if the composition comprises cefepime hydrochloride and tazobactam sodium, the ratio of tazobactam to cefepime is calculated using the equivalent amount of cefepime and tazobactam present in the composition.

In some embodiments, tazobactam in the composition is present as tazobactam sodium.

The amount of the antibacterial agent in the composition can vary depending on the requirements. In some embodiments, the antibacterial agent is present in an amount from about 0.1 to about 10 gram.

In some embodiments, the pharmaceutical composition comprises about 1 gram of the antibacterial agent and about 1 gram of tazobactam.

In some embodiments, the pharmaceutical composition comprises about 2 gram of the antibacterial agent and about 2 gram of tazobactam.

In some embodiments, the pharmaceutical composition comprises about 2 gram of the antibacterial agent and about 1 gram of tazobactam.

In some embodiments, the pharmaceutical composition comprises about 1 gram of the antibacterial agent and about 0.750 gram of tazobactam.

In some embodiments, the pharmaceutical composition comprises about 1 gram of the antibacterial agent and about 0.5 gram of tazobactam.

In another general aspect, there is provided a pharmaceutical composition comprising effective amount of (a) cefepime or a pharmaceutically acceptable salt thereof; and (b) tazobactam or a pharmaceutically acceptable salt thereof, wherein the ratio of tazobactam to cefepime in the composition is in the range of from about 0.5 to about 2 gram of tazobactam per gram of cefepime.

In some embodiments, the pharmaceutical composition comprises about 0.1 to about 10 gram of cefepime.

In some embodiments, the pharmaceutical composition comprises about 1 gram of cefepime and about 1 gram of tazobactam.

In some embodiments, the pharmaceutical composition comprises about 2 gram of cefepime and about 2 gram of tazobactam.

In some embodiments, the pharmaceutical composition comprises about 2 gram of cefepime and about 1 gram of tazobactam.

In some embodiments, the pharmaceutical composition comprises about 1 gram of cefepime and about 0.750 gram of tazobactam.

In some embodiments, the pharmaceutical composition comprises about 1 gram of cefepime and about 0.5 gram of tazobactam.

In another general aspect, there is provided a pharmaceutical composition comprising effective amount of (a) cefpirome or a pharmaceutically acceptable salt thereof; and (b) tazobactam or a pharmaceutically acceptable salt thereof, wherein the ratio of tazobactam to cefpirome in the composition is in the range of from about 0.5 to about 2 gram of tazobactam per gram of cefpirome.

In some embodiments, the pharmaceutical composition comprises about 0.1 to about 10 gram of cefpirome.

In some embodiments, the pharmaceutical composition comprises about 1 gram of cefpirome and about 1 gram of tazobactam.

In some embodiments, the pharmaceutical composition comprises about 2 gram of cefpirome and about 2 gram of tazobactam.

In some embodiments, the pharmaceutical composition comprises about 2 gram of cefpirome and about 1 gram of tazobactam.

In some embodiments, the pharmaceutical composition comprises about 1 gram of cefpirome and about 0.750 gram of tazobactam.

In some embodiments, the pharmaceutical composition comprises about 1 gram of cefpirome and about 0.5 gram of tazobactam.

The pharmaceutical compositions according to the invention may include one or more pharmaceutically acceptable carriers or excipients. Typical, non-limiting examples of such carriers or excipient include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, stabilizing agents, binding agents etc.

The pharmaceutical composition according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols or the like.

In some embodiment, the pharmaceutical composition according to this invention is present in a form of a powder or a solution.

In another general aspect, there are provided methods for treatment or control of bacterial infection using pharmaceutical compositions according to this invention.

In some embodiments, there is provided a method for treatment or control of bacterial infection in a subject, said method comprising administering to said subject a therapeutically effective amount of a pharmaceutical composition according to this invention.

In some embodiments, there is provided a method for treatment or control of bacterial infection in a subject, said method comprising administering to said subject a therapeutically effective amount of a pharmaceutical composition comprising effective amount of (a) at least one antibacterial agent selected from cefepime, cefpirome, ceftobiprole, ceftaroline, cefclidine, cefluprenam, cefoselis, cefozopran, cefquinome, moxalactam, flomoxef, biapenem, panipenem, doripenem, ertapenem, meropenem, imipenem, razupenem, temocillin, CXA-101 or a pharmaceutically acceptable salt thereof; and (b) tazobactam or a pharmaceutically acceptable salt thereof, wherein the ratio of tazobactam to the antibacterial agent in the composition is in the range of from about 0.5 to about 2 gram of tazobactam per gram of the antibacterial agent.

In some embodiments, a pharmaceutical composition comprising effective amount of (a) at least one antibacterial agent selected from cefepime, cefpirome, ceftobiprole, ceftaroline, cefclidine, cefluprenam, cefoselis, cefozopran, cefquinome, moxalactam, flomoxef, biapenem, panipenem, doripenem, ertapenem, meropenem, imipenem, razupenem, temocillin, CXA-101 or a pharmaceutically acceptable salt thereof; and (b) tazobactam or a pharmaceutically acceptable salt thereof, wherein the ratio of tazobactam to the antibacterial agent in the composition is in the range of from about 0.5 to about 2 gram of tazobactam per gram of the antibacterial agent, is used in treatment or control of bacterial infection in a subject.

In some embodiments, there is provided a method for treatment or control of bacterial infection in a subject, said method comprising administering to said subject a therapeutically effective amount of a pharmaceutical composition comprising effective amount of (a) cefepime or a pharmaceutically acceptable salt thereof; and (b) tazobactam or a pharmaceutically acceptable salt thereof, wherein the ratio of tazobactam to cefepime in the composition is in the range of from about 0.5 to about 2 gram of tazobactam per gram of cefepime.

In some other embodiments, a pharmaceutical composition comprising effective amount of (a) cefepime or a pharmaceutically acceptable salt thereof; and (b) tazobactam or a pharmaceutically acceptable salt thereof, wherein the ratio of tazobactam to cefepime in the composition is in the range of from about 0.5 to about 2 gram of tazobactam per gram of cefepime, is used in treatment or control of bacterial infection in a subject.

In some embodiments, there is provided a method for treatment or control of bacterial infection in a subject, said method comprising administering to said subject a therapeutically effective amount of a pharmaceutical composition comprising effective amount of (a) cefpirome or a pharmaceutically acceptable salt thereof; and (b) tazobactam or a pharmaceutically acceptable salt thereof, wherein the ratio of tazobactam to cefpirome in the composition is in the range of from about 0.5 to about 2 gram of tazobactam per gram of cefpirome In some other embodiments, a pharmaceutical composition comprising effective amount of (a) cefpirome or a pharmaceutically acceptable salt thereof; and (b) tazobactam or a pharmaceutically acceptable salt thereof, wherein the ratio of tazobactam to cefpirome in the composition is in the range of from about 0.5 to about 2 gram of tazobactam per gram of cefpirome, is used in treatment or control of bacterial infection in a subject.

In other embodiments, in methods according to this invention, the pharmaceutical composition of according to this invention is administered by any appropriate method, which serves to deliver the composition or its constituents to the desired site. The method of administration can vary depending on various factors, such as for example, the components of the pharmaceutical composition, the site of the potential or actual infection, the microorganism involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash.

The compositions according to the invention comprise tazobactam in combination with another active ingredient (e.g. antibacterial agent, cefepime, cefpirome etc.). A person of skills in the art would appreciate the active ingredients this case can be formulated into various dosage forms wherein tazobactam and the other active ingredient (e.g. antibacterial agent, cefepime, cefpirome etc.) are present either together (mixture) or as a separate components. When the various ingredients in the composition are formulated as a mixture, such composition can be delivered by administering such a mixture. The composition or dosage form wherein the ingredients do not come as a mixture, but come as separate components, such composition/dosage form can be administered in several ways. In one possible way, the ingredients can be mixed in the desired proportions and the mixture is then administered as required. Alternatively, the components can be separately administered in appropriate proportions so as to achieve the same or equivalent therapeutic level or effect as would have been achieved by administration of the equivalent mixture.

In another general aspect, there are provided methods for prophylactic treatment of a subject, comprising administering to a subject at risk of infection caused by bacteria, a prophylactically effective amount a pharmaceutical composition according to the invention.

In general, the pharmaceutical compositions and method disclosed herein are particularly effective against bacteria previously considered to have limited effectiveness against one or more of known antibacterial agents or known compositions. Some non-limiting examples of such bacteria known to have developed resistance to various antibacterial agents include *E. coli, Pseudomonas aeruginosa, Staphylococcus aureus, Enterobacter, Klebsiella, Citrobacter* etc.

A wide variety of microbial infections can be treated using the compositions and method according to this invention.

Examples of bacterial infections which can be treated and/or prevented using the methods and/or the pharmaceutical compositions according to this invention include, without limitation, *E. coli* infections (e.g. urinary tract), *Yersinia pestis* (pneumonic plague), staphyloccal infection, streptococcal infection, mycobacteria infection, bacterial pneumonia, snigella dysentery, serrate infection, candida infection, cryptococcal infection, methicillin resistant *Staphylococcus aureus*, anthrax, tuberculosis or those caused by *Pseudomonas aeruginosa* etc.

The methods and/or compositions according this invention are useful in treating infection caused by *Pseudomonas aeruginosa*, as well as methicillin resistant *Staphylococcus aureus* MRSA, which is one of major causative organisms of nosocomial infections, intra-abdominal and urinary tract infections. Since these bacteria have multi-drug resistance, the treatment of these bacterial infections is difficult, presenting a serious problem in clinical settings.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

The results on activity of cefepime and other cephalosporin antibacterial agents in combination with tazobactam against highly resistant ESBL strains are given Table 1. In a typical study, overnight grown bacterial cultures were diluted appropriately and inoculated on the agar media containing doubling dilutions of the antibiotic. Observation for growth or no growth was performed after 16-20 h of incubation at 35±2° C. in ambient air. The overall procedure was performed as per Clinical and Laboratory Standards Institute (CLSI) recommendations. This experimental was followed for Examples 2-4 and 6 below (Table 2-4 and 7).

Data in Table 1 shows the surprising finding that it is only the combination of cefepime and tazobactam that demonstrates potent activity against high-level resistant ESBL strains. As can be seen from the data in Table 1, such effect was not observed with other tested cephalosporins or their combinations with tazobactam. Typically, the combination of cefepime and tazobactam showed potent inhibition of high level resistant strains thereby bringing down the MICs (increase in potency) of this combination to 2-4 mcg/ml as compared to no inhibition by either cephalosporins or their combination (MICs being 64->128 mcg/ml).

Example 2

The results on activity of cefepime in combination with tazobactam, and penicillins in combination with their respective ESBL inhibitors against highly resistant ESBL strains are given in Table 2.

Data in Table 2 shows surprising finding that it is only the combination of cefepime and tazobactam that is able to demonstrate potent activity against high-level resistant ESBL strains. Typically, the combination of cefepime and tazobactam showed potent inhibition of high level resistant strains thereby bringing down the MICs (increase in potency) of this combination to 2-4 mcg/ml as compared to no inhibition by either penicillin or their combination with tazobactam (MICs being >64 mcg/ml).

Example 3

The results on activity of cefpirome and other cephalosporins in combination with tazobactam against highly resistant ESBL strains are given in Table 3.

Data in Table 3 also confirms the surprising finding that it is only the combination of cefpirome and tazobactam that is able to demonstrate potent activity against high-level resistant ESBL strains. Such effect was not observed with any other cephalosporins or their combination with tazobactam. Typically, the combination of cefpirome and tazobactam showed potent inhibition of high level resistant strains thereby bringing down the MICs (increase in potency) of this combination to 2-8 mcg/ml as compared to no inhibition by either cephalosporins or their combination with MICs being 64->128 mcg/ml.

Example 4

The results on activity of cefpirome in combination with tazobactam, and penicillins in combination with their respective ESBL inhibitors against highly resistant ESBL strains are given in Table 4.

Data in Table 4 shows the surprising finding that it is only the combination of cefpirome and tazobactam that is able to demonstrate potent activity against high-level resistant ESBL strains. Typically, the combination of cefpirome and tazobactam shows potent inhibition of high level resistant strains thereby bringing down the MICs (increase in potency) to 2-4 mcg/ml as compared to no inhibition by either cephalosporins or their combination bringing the MICs at most to >64 mcg/ml.

Example 5

Activity of cefepime in combination with tazobactam and various penicillins in combination with respective ESBL inhibitors was also investigated against highly resistant ESBL strains in quantitative drug diffusion assay performed as per CLSI recommendations (Clinical and Laboratory Standards Institute (CLSI), performance Standards for Antimicrobial Susceptibility Testing, 20th Informational Supplement, M 100—S20, Volume 30, No. 1, 2010).

In a typical study, overnight grown bacterial cultures after appropriate dilution were seed inoculated in the molten, cooled agar media and plates poured. Antibiotics containing 6 mm diameter discs were place on the top of the agar surface. Zone of inhibition based observation was performed after 16-18 h of incubation at 35±2° C. in ambient air. The overall procedure was performed as per CLSI recommendations (Table 5 and 6). These assays are routinely used in determining possibility of treating a particular infection using antibiotic and/or their combinations. For example, in case of treating an infection caused by E. coli (M138) using Augmentien® [commercially available combination: Amoxicillin (500 mg)+Clavulanic acid (125 mg)], the zone inhibition values need to be in the sensitive (S) range. It is generally assumed that the antibiotic or the combination under consideration would not be effective in treating the infection, if the zone inhibition values are in the resistant (R) range.

The CLSI based susceptibility assessment (that guides treatment decisions in an hospital/community setting) of these combinations suggested that, very surprisingly, only the combination of cefepime and tazobactam could convert the susceptibility profile of ESBL strains from 'Resistant' to 'Sensitive' suggesting favorable clinical utility of cefepime-tazobactam combination according to the invention. This is an advantageously surprising result in view of the fact that no other combination, which is currently available, could demonstrate clinically realizable activity against these strains.

A similar study was also undertaken with cefpirome in combination with tazobactam and the results are given in Table 6. Here also, it could be seen that, very surprisingly, only the combination of cefpirome and tazobactam could convert the susceptibility profile of ESBL strains from 'Resistant' to 'Sensitive' suggesting favorable clinical utility of cefpirome-tazobactam combination according to the invention. This is an advantageously surprising result in view of the fact that no other combination, which is currently available, could demonstrate clinically realizable activity against these strains.

Example 6

The results on activity of various ESBL inhibitors such as clavulanic acid, sulbactam and tazobactam in combination with cefepime and cefpirome are given in Table 7. The data in Table 7, clearly and surprisingly shows that antibacterial activity of cefepime and cefpirome was augmented only by the combination with tazobactam and not with other ESBL inhibitors such as clavulanic acid and sulbactam.

The results given in Table 1-7, clearly and surprisingly demonstrate that only specific combinations of antibacterial agents (including cefepime or cefpirome) with tazobactam provide unusual and unexpected synergistic antibacterial effect against high level of ESBL mediated resistant strains. Such significant antibacterial effect was not found when other second or third generation cephalosporins (e.g. cefpodoxime, ceftazidime, ceftriaxone etc.) or penicillins (e.g. amoxicillin, piperacillin, ampicillin, ticarcillin etc.) were combined with any of the currently available ESBL inhibitors (clavulanic acid, tazobactam and sulbactam) at comparable concentrations. Table 5 and 6 provide the proof of concept and demonstrate that it is only the cefepime (0.5 g) or cefpirome (0.5 g) in combination with tazobactam (0.5 g) has tremendous beneficial effect in inhibiting high level resistant ESBL strains demonstrating the noteworthy therapeutic advance in the treatment of infections caused by such pathogenic strains. It is, therefore, conceivable that higher doses of these combinations in the claimed ratio would also lend similar therapeutic gain.

TABLE 1

Activity of cefepime and other cephalosporins in combination with tazobactam against highly resistant ESBL strains

| | | MICs in mcg/ml | | | | | | | | | | | |
|---|---|---|---|---|---|---|---|---|---|---|---|---|---|
| | | Cefpodoxime | | | Ceftriaxone | | | Ceftazidime | | | Cefepime | | |
| Sr. | ESBL Strain | Tazo. (0 mcg) | Tazo. (4 mcg) | Tazo. (8 mcg) | Tazo. (0 mcg) | Tazo. (4 mcg) | Tazo. (8 mcg) | Tazo. (0 mcg) | Tazo. (4 mcg) | Tazo. (8 mcg) | Tazo. (0 mcg) | Tazo. (4 mcg) | Tazo. (8 mcg) |
| 1. | E. cloacae M-20 | >128 | >64 | >64 | >128 | >64 | >64 | >128 | >64 | 64 | >64 | 4 | 4 |
| 2. | E. coli B-89 | >128 | >64 | >64 | >128 | >64 | >64 | >128 | >64 | 64 | >64 | 2 | 2 |
| 3. | E. coli 7MP | >128 | >64 | >64 | >128 | >64 | >64 | >128 | >64 | >64 | >64 | 8 | 4 |
| 4. | E. coli M50 | >128 | >64 | >64 | 128 | 64 | 64 | >128 | >64 | >64 | >64 | 2 | 2 |
| 5. | E. coli B123 | >128 | >64 | >64 | >128 | >64 | >64 | >128 | >64 | >64 | >64 | 4 | 2 |

(Tazo.: Tazobactam)

TABLE 2

Activity of cefepime and penicillins in combination with tazobactam against highly resistant ESBL strains

| | | MICs in mcg/ml | | | | | | | | |
|---|---|---|---|---|---|---|---|---|---|---|
| | | Amoxicillin | | | Piperacillin | | | Ampicillin | | |
| Sr. | ESBL Strain | Tazo. (0 mcg) | Tazo. (4 mcg) | Tazo. (8 mcg) | Tazo. (0 mcg) | Tazo. (4 mcg) | Tazo. (8 mcg) | Tazo. (0 mcg) | Tazo. (4 mcg) | Tazo. (8 mcg) |
| 1. | E. cloacae M-20 | >128 | >64 | >64 | >128 | >64 | >64 | >128 | >64 | >64 |
| 2. | E. coli B-89 | >128 | >64 | >64 | >128 | >64 | >64 | >128 | >64 | >64 |
| 3. | E. coli 7MP | >128 | >64 | >64 | >128 | >64 | >64 | >128 | >64 | >64 |
| 4. | E. coli M50 | >128 | >64 | >64 | >128 | >64 | >64 | >128 | >64 | >64 |
| 5. | K. pneumoniae M150 | >128 | >64 | >64 | >128 | >64 | >64 | >128 | >64 | >64 |

| | | MICs in mcg/ml | | | | | |
|---|---|---|---|---|---|---|---|
| | | Ticarcillin | | | Cefepime | | |
| Sr. | ESBL Strain | Tazo. (0 mcg) | Tazo. (4 mcg) | Tazo. (8 mcg) | Tazo. (0 mcg) | Tazo. (4 mcg) | Tazo. (8 mcg) |
| 1. | E. cloacae M-20 | >128 | >64 | >64 | >64 | 4 | 4 |
| 2. | E. coli B-89 | >128 | >64 | >64 | >64 | 2 | 2 |
| 3. | E. coli 7MP | >128 | >64 | >64 | 32 | 8 | 4 |
| 4. | E. coli M50 | >128 | >64 | >64 | >64 | 2 | 2 |
| 5. | K. pneumoniae M150 | >128 | >64 | >64 | >64 | 4 | 4 |

(Tazo.: Tazobactam)

TABLE 3

Activity of cefpirome and other cephalosporins in combination with tazobactam against highly resistant ESBL strains

| | | MICs in mcg/ml | | | | | | | | | | |
|---|---|---|---|---|---|---|---|---|---|---|---|---|
| | | Cefpodoxime | | | Ceftriaxone | | | Ceftazidime | | | Cefpirome | | |
| Sr. | ESBL Strain | Tazo. (0 mcg) | Tazo. (4 mcg) | Tazo. (8 mcg) | Tazo. (0 mcg) | Tazo. (4 mcg) | Tazo. (8 mcg) | Tazo. (0 mcg) | Tazo. (4 mcg) | Tazo. (8 mcg) | Tazo. (0 mcg) | Tazo. (4 mcg) | Tazo. (8 mcg) |
| 1. | E. cloacae M-20 | >128 | >64 | >64 | >128 | >64 | >64 | >128 | >64 | 64 | >64 | 8 | 4 |
| 2. | E. coli B-89 | >128 | >64 | >64 | >128 | >64 | >64 | >128 | >64 | 64 | >64 | 4 | 2 |
| 3. | E. coli 7MP | >128 | >64 | >64 | >128 | >64 | >64 | >128 | >64 | >64 | >64 | 8 | 4 |
| 4. | E. coli M50 | >128 | >64 | >64 | >128 | >64 | 64 | >128 | >64 | >64 | >64 | 2 | 2 |
| 5. | E. coli B123 | >128 | >64 | >64 | >128 | >64 | >64 | >128 | >64 | >64 | >64 | 4 | 2 |

Tazo.: Tazobactam

TABLE 4

Activity of cefpirome and penicillins in combination with tazobactam against highly resistant ESBL strains

| | | MICs in mcg/ml | | | | | | | | |
|---|---|---|---|---|---|---|---|---|---|---|
| | | Amoxicillin | | | Piperacillin | | | Ampicillin | | |
| Sr. | ESBL Strain | Tazo. (0 mcg) | Tazo. (4mcg) | Tazo. (8 mcg) | Tazo. (0 mcg) | Tazo. (4 mcg) | Tazo. (8 mcg) | Tazo. (0 mcg) | Tazo. (4 mcg) | Tazo. (8 mcg) |
| 1. | E. cloacae M-20 | >128 | >64 | >64 | >128 | >64 | >64 | >128 | >64 | >64 |
| 2. | E. coli B-89 | >128 | >64 | >64 | >128 | >64 | >64 | >128 | >64 | >64 |
| 3. | E. coli 7MP | >128 | >64 | >64 | >128 | >64 | >64 | >128 | >64 | >64 |
| 4. | E. coli M50 | >128 | >64 | >64 | >128 | >64 | >64 | >128 | >64 | >64 |
| 5. | K. pneumoniae M150 | >128 | >64 | >64 | >128 | >64 | >64 | >128 | >64 | >64 |

| | | MICs in mcg/ml | | | | | |
|---|---|---|---|---|---|---|---|
| | | Ticarcillin | | | Cefepime | | |
| Sr. | ESBL Strain | Tazo. (0 mcg) | Tazo. (4 mcg) | Tazo. (8 mcg) | Tazo. (0 mcg) | Tazo. (4 mcg) | Tazo. (8 mcg) |
| 1. | E. cloacae M-20 | >128 | >64 | >64 | >64 | 8 | 4 |
| 2. | E. coli B-89 | >128 | >64 | >64 | >64 | 4 | 2 |
| 3. | E. coli 7MP | >128 | >64 | >64 | 32 | 8 | 4 |
| 4. | E. coli M50 | >128 | >64 | >64 | >64 | 2 | 2 |
| 5. | K. pneumoniae M150 | >128 | >64 | >64 | >64 | 4 | 4 |

Tazo.: Tazobactam

TABLE 5

Activity of cefepime with tazobactam, and various penicillins with their respective ESBL inhibitors against highly resistant ESBL strains (as per CLSI recommendations).

| | | Zone of Inhibition (mm) for representative product combinations | | | | | | | | | |
|---|---|---|---|---|---|---|---|---|---|---|---|
| | | Amoxicillin [a] | | Piperacillin [b] | | Ampicillin [c] | | Ticarcillin [d] | | Cefepime [e] | |
| Sr. | ESBL Strain | Clav. (0 mcg) | Clav. (10 mcg) | Tazo. (0 mcg) | Tazo. (10 mcg) | Sulb. (0 mcg) | Sulb. (10 mcg) | Clav. (0 mcg) | Clav. (10 mcg) | Tazo. (0 mcg) | Tazo. (10 mcg) |
| 1. | E. coli M-138 | Nil (R) | Nil (R) | Nil (R) | 15.5 (R) | Nil (R) | Nil (R) | Nil (R) | 10 (R) | Nil (R) | 23 (S) |
| 2. | E. coli B-89 | Nil (R) | Nil (R) | Nil (R) | 15 (R) | Nil (R) | Nil (R) | Nil (R) | 10 (R) | 8 (R) | 20 (S) |
| 3. | E. coli B-123 | Nil (R) | Nil (R) | Nil (R) | 13.5 (R) | Nil (R) | Nil (R) | Nil (R) | 13.5 (R) | 8 (R) | 20 (S) |
| 4. | E. coli M50 | Nil (R) | Nil (R) | Nil (R) | 17 (R) | Nil (R) | Nil (R) | 9 (R) | 11.5 (R) | 7.5 (R) | 24 (S) |
| 5. | E. coli 7MP | Nil (R) | Nil (R) | Nil (R) | 13.5 (R) | Nil (R) | Nil (R) | Nil (R) | Nil (R) | 16 (I) | 20.5 (S) |
| 6. | E. coli S-112 | Nil (R) | Nil (R) | Nil (R) | 14 (R) | Nil (R) | Nil (R) | Nil (R) | 10 (R) | 17 (I) | 20.5 (S) |

R: Resistant;
I: Intermediate;
S: Sensitive (Interpretation as per CLSI recommendations, 2010)
Clav.: Clavulanic acid;
Tazo.: Tazobactam;
Sulb.: Sulbactam
[a] for possible treatmentwith Augmentin ®[Amoxicillin (500 mg) + Clavulanic acid (125 mg)];
[b] for possible treatmentwith Zosyn ® [Piperacillin (4 g) + Tazobactam (500 mg)];
[c] for possible treatmentwith Unasyn ® [Ampicillin (2 g) + Sulbactam (1 g)];
[d] for possible treatmentwith Timentin ® [Ticarcillin (3 g) + Clavulanic acid (100 mg)];
[e] for possible treatmentwith Cefepime (0.5 g) + Tazobactam (0.5 g).

TABLE 6

Activity of cefpirome with tazobactam, and various penicillins with their respective ESBL inhibitors against highly resistant ESBL strains (as per CLSI recommendations).

| | | Zone of Inhibition (mm) for representative product combinations | | | | | | | | | |
|---|---|---|---|---|---|---|---|---|---|---|---|
| | | Amoxicillin [a] | | Piperacillin [b] | | Ampicillin [c] | | Ticarcillin [d] | | Cefpirome [e] | |
| Sr. | ESBL Strain | Clav. (0 mcg) | Clav. (10 mcg) | Tazo. (0 mcg) | Tazo. (10 mcg) | Sulb. (0 mcg) | Sulb. (10 mcg) | Clav. (0 mcg) | Clav. (10 mcg) | Tazo. (0 mcg) | Tazo. (10 mcg) |
| 1. | E. coli M-138 | Nil (R) | Nil (R) | Nil (R) | 15.5 (R) | Nil (R) | Nil (R) | Nil (R) | 10 (R) | Nil (R) | 21 (S) |
| 2. | E. coli B-89 | Nil (R) | Nil (R) | Nil (R) | 15 (R) | Nil (R) | Nil (R) | Nil (R) | 10 (R) | Nil (R) | 17.5 (S) |
| 3. | E. coli B-123 | Nil (R) | Nil (R) | Nil (R) | 13.5 (R) | Nil (R) | Nil (R) | Nil (R) | 13.5 (R) | 8 (R) | 20 (S) |
| 4. | E. coli M50 | Nil (R) | Nil (R) | Nil (R) | 17 (R) | Nil (R) | Nil (R) | 9 (R) | 11.5 (R) | Nil (R) | 22 (S) |
| 5. | E. coli 7MP | Nil (R) | Nil (R) | Nil (R) | 13.5 (R) | Nil (R) | Nil (R) | Nil (R) | Nil (R) | 11 (R) | 18.5 (S) |
| 6. | E. coli S-112 | Nil (R) | Nil (R) | Nil (R) | 14 (R) | Nil (R) | Nil (R) | Nil (R) | 10 (R) | 15 (I) | 20 (S) |

R: Resistant;
I: Intermediate;
S: Sensitive (Interpretation as per CLSI recommendations, 2010)
Clav.: Clavulanic acid;
Tazo.: Tazobactam;
Sulb.: Sulbactam
[a] for possible treatment with Augmentin ® [(Amoxicillin (500 mg) + Clavulanic acid (125 mg)];
[b] for possible treatment with Zosyn ® [Piperacillin (4 g) + Tazobactam (500 mg)];
[c] for possible treatment with Unasyn ® [Ampicillin (2 g) + Sulbactam (1 g)];
[d] for possible treatment with Timentin ® [Ticarcillin (3 g) + Clavulanic acid (100 mg)];
[e] for possible treatment with Cefpirome (0.5 g) + Tazobactam (0.5 g).

TABLE 7

Activity of various ESBL-inhibitors (clavulanic acid, sulbactam and tazobactam) in combination with cefepime and cefpirome

| | | Cefepime | | | | | | | Cefpirome | | | | | | |
|---|---|---|---|---|---|---|---|---|---|---|---|---|---|---|---|
| Sr. | ESBL Strain | Cefepime alone | Clav. (4 mcg) | Clav. (8 mcg) | Sulb. (4 mcg) | Sulb. (8 mcg) | Tazo. (4 mcg) | Tazo (4 mcg) | Cefpirome alone | Clav. (4 mcg) | Clav. (8 mcg) | Sulb. (4 mcg) | Sulb. (8 mcg) | Tazo. (4 mcg) | Tazo (4 mcg) |
| 1. | E. cloacae M-20 | >64 | 16 | 8 | 32 | 16 | 4 | 4 | >64 | 16 | 8 | 32 | 16 | 8 | 4 |
| 2. | E. coli B-123 | >64 | 8 | 8 | 8 | 16 | 4 | 2 | >64 | 16 | 8 | 8 | 16 | 4 | 2 |
| 3. | E. coli 7MP | >64 | 16 | 8 | 16 | 16 | 8 | 4 | >64 | 16 | 8 | 16 | 16 | 8 | 4 |

Clav.: Clavulanic acid;
Tazo.: Tazobactam;
Sulb.: Sulbactam

The invention claimed is:

1. A pharmaceutical composition comprising active ingredients consisting of (a) cefepime or a pharmaceutically acceptable salt thereof; and (b) tazobactam or a pharmaceutically acceptable salt thereof, wherein the composition comprises 2 grams of cefepime and 2 grams of tazobactam, and is capable of treating bacterial infection in a subject.

2. The pharmaceutical composition according to claim 1, wherein the tazobactam is present as tazobactam sodium.

3. The pharmaceutical composition according to claim 1, wherein the composition is a powder or a solution.

\* \* \* \* \*